Figure 1:
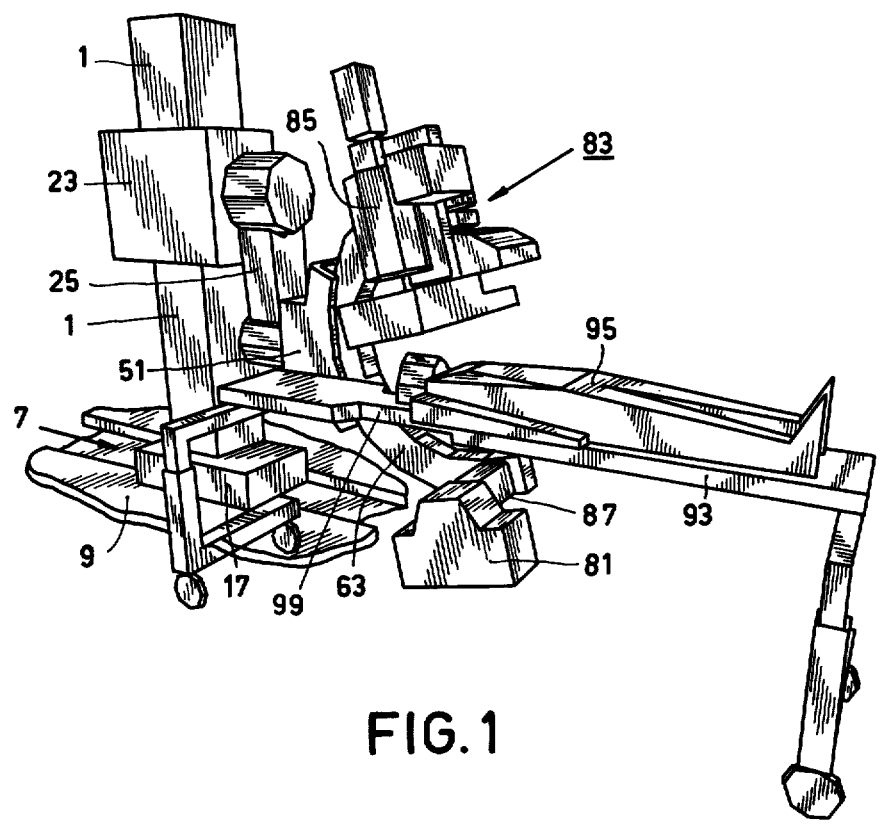

United States Patent [19]

Janssen et al.

[11] Patent Number: 4,481,656
[45] Date of Patent: Nov. 6, 1984

[54] MEDICAL APPARATUS

[75] Inventors: Jozef T. A. Janssen; Antonius W. M. Schijvens, both of Eindhoven, Netherlands

[73] Assignee: U.S. Philips Corporation, New York, N.Y.

[21] Appl. No.: 374,805

[22] Filed: May 4, 1982

[30] Foreign Application Priority Data

May 11, 1981 [NL] Netherlands .................. 8102286

[51] Int. Cl.³ .................................. C03B 41/16
[52] U.S. Cl. .................................. 378/196; 378/210
[58] Field of Search .......................... 378/196, 197

[56] References Cited

U.S. PATENT DOCUMENTS 4,209,706  6/1980  Nunan ........................ 378/197

Primary Examiner—Craig E. Church
Attorney, Agent, or Firm—Norman N. Spain

[57] ABSTRACT

A medical apparatus comprising a displaceable vertical column 1 along which there can be slid a support 23 in which an arm 25 is rotatable about a first horizontal axis. Secured to the arm 25 and rotatable about a second horizontal axis parallel to the first horizontal axis, is an examination device which comprises a combination of a radiation source 81 and a radiation detector 83. Said combination is mounted on a C-shaped frame 63 which is displaceable circumferentially about an axis which lies at right angles to both horizontal axes. The two translatory displacements and the three rotary displacements of the apparatus can be performed individually by means of corresponding variable speed motor drives whose operation can, however, be coordinated if desired.

The medical apparatus is particularly suitable for so-called isocentric examinations of the vascular system.

4 Claims, 11 Drawing Figures

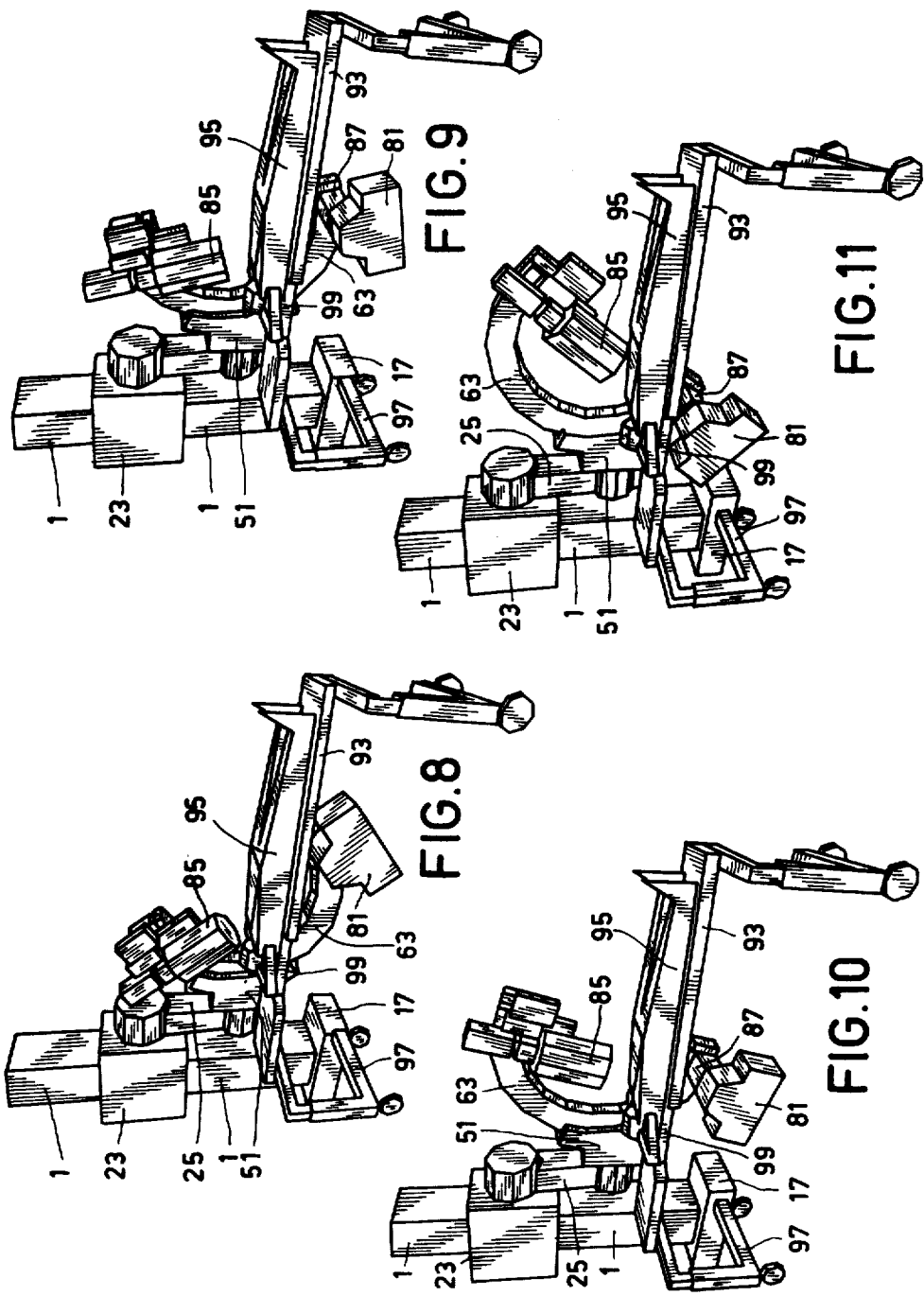

MEDICAL APPARATUS

The invention relates to a medical apparatus, comprising a vertical column which is displaceable along a horizontal rectilinear displacement path, a support which is slidable along said column in a vertical direction, and an arm which is journalled in said support so as to be rotatable about a first horizontal axis parallel to the displacement path of the column, and is arranged to carry a supporting bearing for an examination device which latter is thereby made rotatable about a second horizontal axis which is parallel to the first horizontal axis, and such apparatus will be referred to herein as apparatus of the kind specified.

In a known medical apparatus of the kind set forth (German Gebrauchsmuster No. 1,858,366), the examination device which is rotatable about the second horizontal axis consists of an auxiliary apparatus such as, for example, an X-ray film cassette. It will be apparent that, instead of using solely an X-ray film cassette, use can be made of an examination device which is formed by the combination of a radiation source and a radiation detector, for example, an X-ray source and an X-ray image intensifier. Depending on how such a combination of radiation source and radiation receiver is suspended in the medical apparatus, the apparatus will be more or less suitable for given types of medical examination.

It is to be noted that medical apparatus for performing so-called isocentric examinations are known per se (U.S. Pat. No. 3,281,598). Apparatus of this kind, however, imposes restrictions as regards the choice of the isocentre. This is because the isocentre is always situated at the intersection of the horizontal and the vertical axis of rotation at the centre of a circular frame, so that structural members will be present at locations which it would be convenient for the patient or the operator to occupy. The freedom of movement of the patient or the operator is thus substantially reduced.

It is an object of the invention to provide an improved medical apparatus which is suitable for performing so-called isocentric examination, for example, examination of the blood vessels of the head, heart, liver and kidneys, in which the freedom of movement of patient and operator can be made comparatively great.

According to the invention there is provided a medical apparatus, comprising a vertical column which is displaceable along a horizontal rectilinear displacement path, a support which is slidable along said column in a vertical direction, and an arm which is journalled in said support so as to be rotatable about a first horizontal axis parallel to the displacement path of the column, and is arranged to carry a supporting bearing for an examination device which latter is thereby made rotatable about a second horizontal axis which is parallel to the first horizontal axis, characterized in that the examination device comprises an assembly formed by a radiation source and a radiation detector mounted on a C-shaped frame which latter is displaceably supported by a support bracket which is journalled in said supporting bearing so as to be rotatable about the second horizontal axis, said support bracket including bearing means arranged to engage the C-shaped frame so that the latter is made displaceable circumferentially with respect to the support bracket along a circular displacement path whose median plane extends parallel to both said horizontal axes, said assembly being arranged so that the central ray axis of the examination device lies in a plane which is spaced from a notional plane defining the adjacent boundary of the C-shaped frame and is parallel to the median plane of the circular displacement path, each of said translatory and rotary displacements being respectively provided by a corresponding individual variable speed motor drive.

The number and the kind (translation or rotation) of degrees of freedom of movement embodied in a medical apparatus in accordance with the invention can enable any point in the body of a patient to be examined from a comparatively large number of directions, if desired, with a constant magnification factor. This is first of all due to the fact that a patient can be positioned with respect to the medical apparatus so that the body axis extends parallel to both horizontal axes and the median plane of the displacement path of the C-shaped frame, while the central ray axis is situated parallel to and at some distance from said median plane. This can be illustrated by an examination of blood vessels in the legs of a patient which can be executed by displacement of the column along the direction of the body axis.

The number of points in the body of a patient which can be irradiated or examined from a number of directions (the so-called isocentric point), moreover, will be restricted only to a comparatively small extent by the construction of medical apparatus in accordance with the invention. For example, it will not be necessary to limit the examination to points lying in the plane of the C-shaped frame or lying on the axes of rotation of the medical apparatus.

In one embodiment of a medical apparatus in accordance with the invention, the assembly formed by the combination of a C-shaped frame, a radiation source and a radiation detector, is arranged to exert a minimum torque about an axis through the centre M of the circular displacement path which extends perpendicularly to the median plane of the circular displacement path.

An advantage thereof is that the motor drive employed to rotate the C-shaped frame with respect to the support bracket may have a comparatively light construction. To achieve this, such a medical apparatus is characterized in that the C-shaped frame has a rotation axis which passes through the centre M of the circular displacement path of the C-shaped frame is situated at a distance a from the second horizontal axis and at a distance b from the central ray axis which is parallel to a diameter of the circular displacement path and which is spaced with respect to this diameter by the distance b in the direction of the open side of the C-shaped frame, a and b being defined so that the mean centre of gravity of the assembly formed by the C-shaped frame, the radiation source and the radiation detector, is situated substantially on a notional line which extends through the centre M of the circular displacement path in a direction perpendicular to the median plane of the circular displacement path.

Another embodiment of a medical apparatus in accordance with the invention offers the advantage that it can have comparatively small principal dimensions; notably the length of the arm can be made comparatively short because the focal spot of the radiation source is situated at a distance $p+a$ along the central ray axis from a plane at right angles thereto which includes the rotation axis of the C-shaped frame passing through the centre M of the circular displacement path, in which a is the distance between the rotation axis of the C-shaped frame and the second horizontal axis and p is equal to half the sum of the corresponding distances between the focal spot and the isocentre during an exposure with the largest magnification factor and an exposure with the smallest magnification factor, respectively.

For practical applications of the apparatus it is advantageous to have also a manual operation facility available. To this end, a combination of components to be displaced should be mounted in a balanced manner. For angular displacement, the centre of gravity of the combination formed by the C-shaped frame, the source and the image intensifier, therefore, is made to coincide with the centre of rotation of the C-shaped frame, for example, by addition of extra weight to the C-shaped frame. For rotation, the centre of gravity of the combination formed by the C-shaped frame, the source, the image intensifier and the counterweight is made to coincide with the centre of rotation of this combination. To this end it is also ensured that the axis of rotation extends through this centre of rotation.

Because the C-shaped frame should not simply rotate about its centre of rotation during an examination but rather about the isocentric point of the source and image intensifier tube axis, there is provided a level translatory displacement control facility for angular displacement and a rotation β level displacement control facility for rotation. The relevant control data are derived from the position and the speed of the relevant components in order to be combined, for example, in a computer or microprocessor, to form a control signal for control of the speed and the position of these components. It is thus ensured that rotation always takes place about the isocentric point, without collision of components.

Figure 2:
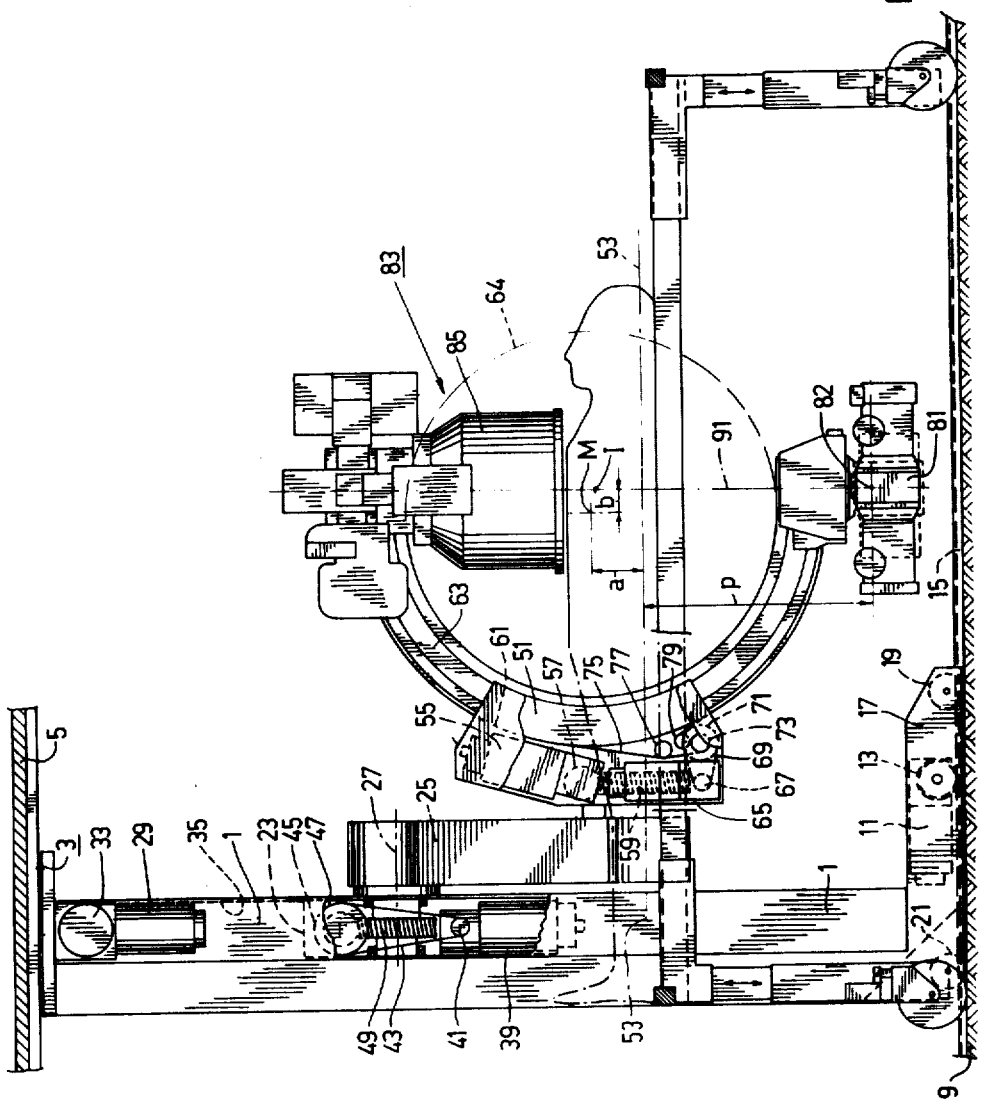
Figure 3:
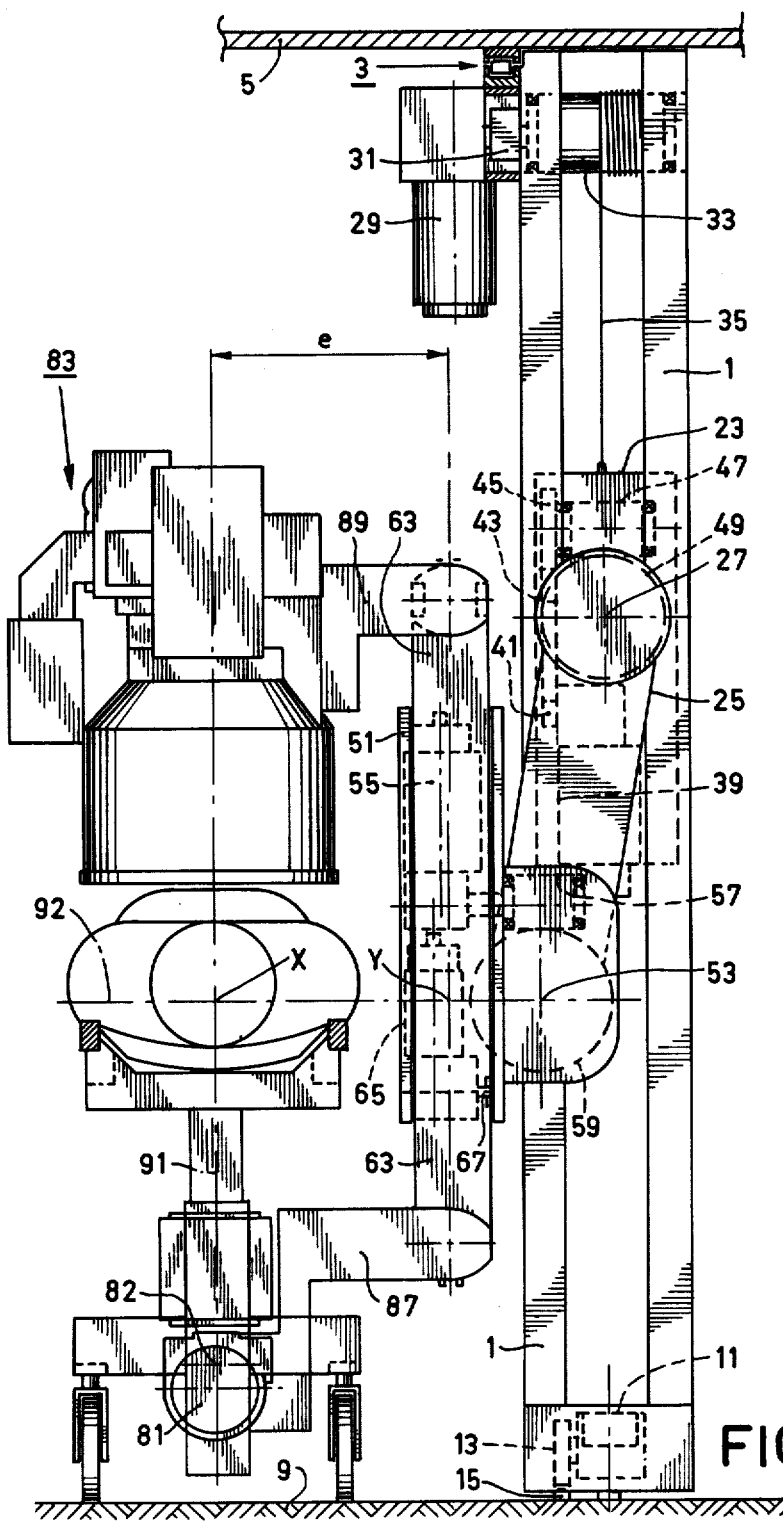
Figure 4:
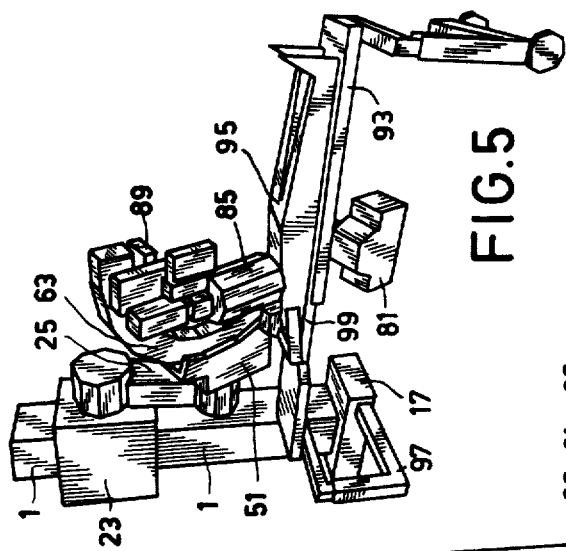
Figure 5:
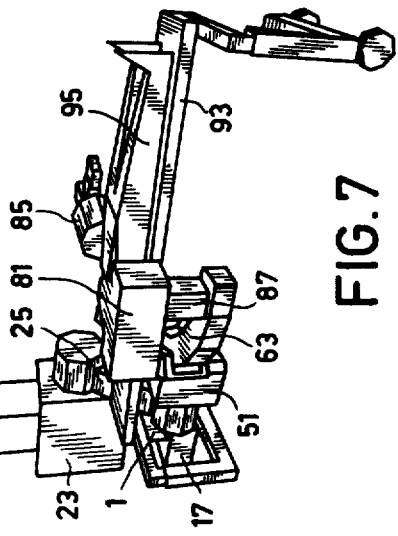

An embodiment of the invention will now be described by way of example, with reference to the accompanying drawings, of which:

FIG. 1 is a diagrammatic perspective view of one embodiment of a medical apparatus in accordance with the invention, FIG. 2 is a side elevation of a medical apparatus as illustrated in FIG. 1, FIG. 3 is an enlarged front view of the medical apparatus shown in FIG. 2, FIGS. 4, 5, 6 and 7 show the medical apparatus of FIG. 1, and illustrate possible examination positions, the C-shaped frame each time being in the same orientation with respect to the supporting bracket, and FIGS. 8, 9, 10 and 11 show the medical apparatus of FIG. 1 and illustrate further possible examinations positions, the C-shaped frame occupying different orientations with respect to the supporting bracket.

The medical apparatus shown in FIGS. 1, 2 and 3, comprises a vertical column 1 which is horizontally displaceable in a vertical plane (the plane of the drawing in FIG. 2). The column 1 is displaceable along horizontal rectilinear guides 3 in a ceiling 5 (see FIGS. 2 and 3) and horizontal rectilinear guides 7 in a floor 9 by means of a motor drive 11. On the drive shaft of the motor drive 11 there is secured a toothedwheel 13 which engages a comparatively long toothed rack 15 (approximately 4 m long) which is arranged on the floor 9. The motor drive 11 is accomodated in a base 17 of the vertical column 1. The base 17 also comprises a pair of front wheels 19 and a pair of rear wheels 21 which roll on the floor 9.

A support 23 is slidable along (i.e. up and down) the vertical column 1, an arm 25 which is rotatable about a first horizontal axis 27 being journalled in said support.

The support 23 is displaced by means of a motor drive 29. Via a coupling 31 (see FIG. 3), the drive shaft of the motor drive can be coupled to a drum 33 which is journalled in the column 1 and around which a cable 35, connected to the support 23, can be wound and unwound. The arm 25 is driven by means of a motor drive 39 which is fixedly arranged in the support 23. A pulley 41 on the drive shaft of the motor drive 39 is coupled to a pulley 45 by means of a drive belt 43. The pulley 45 is secured on a shaft which also supports a worm gear 47 which engags a wormwheel 49. The wormwheel 49 is mounted on the arm 25 which is rotatably journalled in the support 23, the center of the wormwheel 49 being coincident with the first horizontal axis 27.

A support bracket 51 is journalled in the arm 25. The support bracket 51 is rotatable about a second horizontal axis 53 which is parallel to the first horizontal axis 27. The axes 27 and 53 are parallel to the rectilinear displacement path followed by the column 1 in the guides 3 and 7. The support bracket 51 can be rotated with respect to the arm 25 by means of a motor drive 55 which is fixedly arranged in the support bracket 51. On the drive shaft of the motor drive 55 there is mounted a wormgear 57 which engages a wormwheel 59. The wormwheel 59 is secured to the arm 25, the centre of the wormwheel 59 being coincident with the second horizontal axis 53. The support bracket 51 includes bearing means comprising a guide 61 having the form of a circular arc (diagrammatically shown in FIG. 2 for the sake of simplicity). In the guide 61 a C-shaped frame 63 is slidable along its circumference with the assistance of rollers (not shown) if desired so as to follow a circular displacement path 64. The median plane of the circular displacement path 64, is parallel to both the horizontal axes 27 and 53. The C-shaped frame 63 is shaped as an arc of a cricle which extends over approximately a semi circle. The open side of the C-shaped frame 63 is remote from the column 1 in FIG. 2. The frame 63 is displaced relative to the support bracket 51 by means of a motor drive 65 which is fixedly arranged in the support bracket 51. On the drive shaft of the motor drive 65 there is mounted a pulley 67 which is coupled to a further pulley 71 by means of a drive belt 69. The pulley 71 is mounted on a shaft on which there is also mounted a chain pinion 73 which engages a chain 75 which is guided along the frame 63. Guide wheels 77 and 79 serve further to guide the chain 75, the ends of which are secured to the frame 63.

The present examination device consists of a combination of a radiation source 81 and a radiation detector 83 which are centred with respect to one another. For the radiation source 81 use is made of an X-ray source having a focal spot 82, whilst the radiation detector 83 comprises inter alia an X-ray image intensifier 85. The radiation source 81 is secured to the frame 63 by means of a transverse arm 87, the radiation detector 83 being secured to the frame 63 by means of a transverse arm 89. A so-called central ray axis 91 of the examination device, is therefore, spaced by a distance e from the median plane 66 (FIG. 3) of the circular displacement path 64. The central ray 91 will always be parallel to the median plane of the circular displacement path 64. The rotation axis of the frame 63, which passes through the centre M of the circular displacement path 64, is situated at a distance a from the second horizontal axis 53. The radiation detector 83 is displaceable with respect to the frame 63 in a direction along the central ray axis 91, so that the distance between the radiation detector 83 and the radiation source 81 which is rigidly connected to the frame 63 can be adjusted, for example, in order to vary the focal spot to film distance. Because the respective centres of gravity of the C-shaped frame 63 and of the examination device (i.e. the radiation source 81 and the radiation detector 83) are situated in different positions with respect to the frame 63 during the various types of examinations or exposures and because, moreover, examination devices of different weight are often used, the distance a (see FIG. 2) is chosen so that, viewed along the direction of the central ray axis 91, the mean centre of gravity in the various circumstances is substantially coincident with a line through the rotation centre M of the C-frame 63 (circular) which is perpendicular to the median plane 66 of the circular displacement path 64. The distance b between the central ray axis 91 and the rotation centre M is also chosen so that the mean centre of gravity in said different situations, is substantially coincident, viewed in a direction perpendicular to the central ray axis, with a line through the centre M of the C-frame 63 which is perpendicular to the median plane of the circular displacement path 64. Viewed in FIG. 3, the centre of gravity of the assembly formed by the C-frame 63, the radiation source 81 and the radiation detector 83 on average should be situated on the line 92 between the points X and Y.

The distance p between the focal spot 82 and the second horizontal axis 53 in the orientation shown in FIG. 2, equals half the sum of the corresponding distances between on the one hand the focal spot 82 and the isocentre I at maximum magnification and on the other hand the focal spot 82 and the isocentre I at minimum magnification. FIG. 2 shows the situation at minimum magnification (so-called contact exposure). When the distance p is chosen in the described manner, notably a comparatively small length of the arm 25 suffices, whilst the range of the arm is still sufficient. It will be readily apparent that the focal spot is, in general, situated at a distance p+a along the central ray axis from a plane at right angles thereto which includes the rotation axis of the C-shaped frame 63 passing through the centre M.

In the embodiment shown:
a = 150 mm
b = 70 mm
p = ½ (450+900) = 675 mm.

The five variable speed motor drives 11, 29, 39, 55 and 65 are preferably formed by variable speed electric motors which can be controlled so that, if desired, while using the same radiographic magnification factor, the central ray axis 91 can be directed in succession along a large number of different directions through a given point (isocentre) in a patient 95 under examination arranged on a patient table 93. To achieve this, known control circuits can be used for example, of the type described in U.S. Pat. No. 4,019,059. However, it is not always necessary to utilize all the degrees of freedom provided by the apparatus in combination at any given instant (i.e. at the same time). Many kinds of diagnostic examinations require a sequential execution of respective displacements, for example, first a translation of the column 1 and subsequently a displacement of the frame 63 in the bearing segment 61.

In order to suggest the range of examination possibilities offered by the described medical apparatus, reference is made to the diagrammatic FIGS. 4, 5, 6 and 7 which have been produced by means of a computer and which simulate the various examination positions. Starting from the position shown in FIG. 4 in which the stationary patient 95 is irradiated in the horizontal direction through a given point in the thorax, the irradiation direction is changed so that the central ray axis is always situated in the same vertical plane at right angles to the body axis of the patient 95, whilst the magnification factor is maintained constant. Two of the five degrees of freedom remain unused during this type of isocentric examination, i.e. the horizontal translatory movement of the column 1 and the rotation of the frame 63 in the support bracket 51. This can be readily seen by comparison of the mutual positions of a transverse leg 97 of the patient table 93 and the base 17 in the FIGS. 4-6 and the mutual positions of the support bracket 51 and the frame 63. The patient table 93 is arranged to be stationary. The FIGS. 4, 5, 6 and 7 show that rotation of the frame 63 through one hundred and eighty degrees is possible (see FIGS. 4 and 7), so that all the diagnostically relevant irradiation directions in a plane at right angles to the body axis of the patient can in fact be used. The patient table 93 is provided with a cut-out 99 so that so-called contact images of, for example, the head of a patient can be obtained (see FIGS. 5 and 4).

The FIGS. 8, 9, 10 and 11 which have also been obtained by means of a computer, illustrate that a large number of diagnostically relevant irradiation directions can also be achieved with a constant magnification factor in a vertical plane parallel to the body axis of the patient. For the examination illustrated by the FIGS. 8 to 11 not all the available degrees of freedom are used either. By comparison of the mutual positions of the base 17 and the transverse leg 97, it can be seen that the translatory movement of the column 1 is used (the patient table 93 occupies a fixed position). It is clearly shown that the translatory movement of the support 23 is also used, and also the rotation of the frame 63 in the support bracket 51. The rotary movement of the arm 25 with respect to the support 23 and the rotary movement of the support bracket 51 with respect to the arm 25 are not necessary for the described examination.

Figure 6:
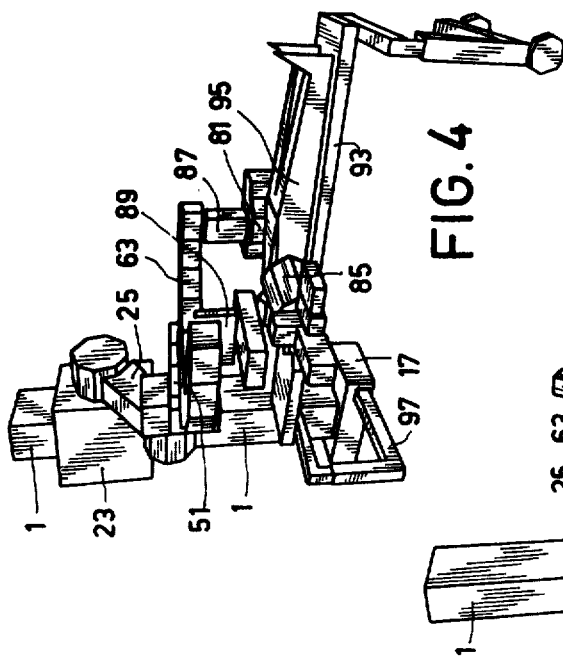
Figure 7:
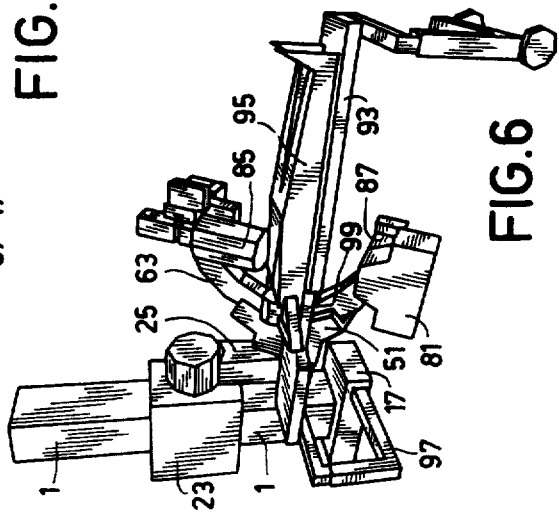

All five degrees of freedom are simultaneously utilized when, for example, the frame 63 is rotated in the support bracket 51 from the positions shown in FIG. 6 with a constant magnification factor and a constant angle between the column 1 and the plane of the circular displacement path 64.

Even though the described medical apparatus comprises a circular frame 63, use can alternatively be made of a C-shaped or U-shaped frame. The circular frame, however, offers the advantage that it has a comparatively simple construction with a comparatively large angle of rotation of the frame 63 with respect to the support bracket 51.

Finally, it is to be noted that the medical apparatus is not restricted to so-called isocentric examinations, even though it is particularly suitable for such type of examination.

What is claimed is:

1. A medical apparatus, comprising a vertical column which is displaceable along a horizontal rectilinear displacement path, a support which is slidable along said column in a vertical direction, and an arm which is journalled in said support so as to be rotatable about a first horizontal axis parallel to the displacement path of the column, and is arranged to carry a supporting bearing for an examination device which latter is thereby made rotatable about a second horizontal axis which is parallel to the first horizontal axis, characterized in that the examination device comprises an assembly formed by a radiation source and a radiation detector mounted on a C-shaped frame which latter is displaceably supported by a support bracket which is journalled in said supporting bearing so as to be rotatable about the second horizontal axis, said support bracket including bearing means arranged to engage the C-shaped frame so that the latter is made displaceable circumferentially with respect to the support bracket along a circular displacement path whose median plane extends parallel to both said horizontal axes, said assembly being arranged so that the central ray axis of the examination device lies in a plane which is spaced from a notional plane defining the adjacent boundary of the C-shaped frame and is parallel to the median plane of the circular displacement path, each of said translatory and rotary displacements being respectively provided by a corresponding individual variable speed motor drive.

2. A medical apparatus as claimed in claim 1, characterized in that the C-shaped frame has a rotation axis which passes through the centre M of the circular displacement path of the C-shaped frame is situated at a distance a from the second horizontal axis and at a distance b from the central ray axis which is parallel to a diameter of the circular displacement path and which is spaced with respect to this diameter by the distance b in the direction of the open side of the C-shaped frame, a and b being defined so that the mean centre of gravity of the assembly formed by the C-shaped frame, the radiation source and the radiation detector is situated substantially on a notional line which extends through the centre M of the circular displacement path in a direction perpendicular to the median plane of the circular displacement path.

3. A medical apparatus as claimed in claim 1 or 2, characterized in that the focal spot of the radiation source is situated at a distance $p+a$ along the central ray axis from a plane at right angles thereto which includes the rotation axis of the C-shaped frame passing through the centre M of the circular displacement path, in which a is the distance between the rotation axis of the C-shaped frame and the second horizontal axis and p is equal to half the sum of the corresponding distances between the focal spot and the isocentre during an exposure with the largest magnification factor and an exposure with the smallest magnification factor, respectively.

4. A medical apparatus as claimed in claim 1, characterized in that the angular displacement system is balanced by making the relevant centre of gravity coincide with the centre of rotation of the C-shaped frame.

* * * * *